US011578122B2

(12) United States Patent
Bhambure et al.

(10) Patent No.: US 11,578,122 B2
(45) Date of Patent: *Feb. 14, 2023

(54) IPTG-FREE INDUCTION PROCESS FOR EXPRESSION OF BIOSIMILAR RHU RANIBIZUMAB ANTIBODY FRAGMENT USING E. COLI

(71) Applicant: COUNCIL OF SCIENTIFIC & INDUSTRIAL RESEARCH, New Delhi (IN)

(72) Inventors: Rahul Sharad Bhambure, Pune (IN); Aatir Asad Tungekar, Pune (IN); Deepa Mehta, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 74 days.

This patent is subject to a terminal disclaimer.

(21) Appl. No.: 16/775,811

(22) Filed: Jan. 29, 2020

(65) Prior Publication Data

US 2020/0165332 A1  May 28, 2020

Related U.S. Application Data

(63) Continuation of application No. 16/685,041, filed on Nov. 15, 2019, which is a continuation-in-part of application No. PCT/IN2018/050315, filed on May 18, 2018.

(30) Foreign Application Priority Data

May 19, 2017 (IN) .............................. 201711017654

(51) Int. Cl.
C07K 16/22 (2006.01)
(52) U.S. Cl.
CPC .......... C07K 16/22 (2013.01); C07K 2317/24 (2013.01)
(58) Field of Classification Search
CPC ............................ C07K 16/22; C07K 2317/24
See application file for complete search history.

(56) References Cited

U.S. PATENT DOCUMENTS

2008/0125580 A1  5/2008  Pizarro et al.
2016/0289314 A1  10/2016  Shandlya et al.

FOREIGN PATENT DOCUMENTS

| CN | 102757496 A | 10/2012 |
| WO | WO9845331 | 10/1998 |
| WO | WO2013076657 | 5/2013 |
| WO | WO2014178078 | 11/2014 |
| WO | WO2016005931 | 1/2016 |

OTHER PUBLICATIONS

Xu et al., Protein Expression and Purification 83 (1): 30-36 (2012).*
Donovan, et al., "Optimizing the expression of a monoclonal antibody fragment under the transcriptional control of the *Escherichia coli* lac promoter" Can. J. Microbiol. 46: 532-541 (2000).
PCT Search Report and Written Opinion dated Jul. 16, 2018 issued for International PCT Application No. PCT/IN2018/050315.
Singh et al. "Solubilization and refolding of bacterial inclusion body proteins", Journal of Bioscience and Bioengineering, Amsterdam, NL, vol. 99, No. 4, Apr. 2005, pp. 303-310.
Nelson A. and Reichert J. Development trends for therapeutic antibody fragments. Nature biotechnology 2009, 27, No. 4.
Nelson A., Antibody fragments Hope and hype. MAbs, 2010, 2:1, 77-83.
Clark EDB., Protein refolding for industrial processes. Current Opinion in Biotechnology, 2001, 12(1): 202-207.
Jungbauer A., Kaar W., Current status of technical protein refolding. Journal of Biotechnology, 2007, 128(3): 587-596.
Middelberg APJ., Preparative protein refolding. Trends in Biotechnology, 2002, 20(10), 437-443.
Hannig G. and Makrides S. Strategies for optimizing heterologous protein expression in *Escherichia coli.* Trends in Biotechnolgy, 1998, 16, 54-60.
Corisdeo S. and Wang B. Functional expression and display of an antibody Fab fragment in *Escherichia coli:* study of vector designs and culture conditions. Protein Expression and Purification 2004, 34, 270-279.
Humphreys D., Carrington B., Bowering L., Ganesh R,, Sehdev M., Smith B., King L., Reeks D, Lawson A and Popplewell A. A plasmid system for optimization of Fab production in *Escherichia coli:* importance of balance of heavy chain and light chain synthesis. Protein Expression and Purification 2002, 26, 309-320.
O'Brien Ph., Maxwell G., and Campo M. Bacterial Expression and Purification of Recombinant Bovine Fab Fragments. Protein Expression and Purification 2002, 24, 43-50.
Carter P., Kelley R., Rodrigues M., Snedecor B., Covarrubias M., Velligan M., Wong W., Rowland A., Kotts C., Carver M., Yang M., Bourell J., Shepard H. and Henner D. High Level *Escherichia coli* Expression and Production of a Bivalent Humanized Antibody Fragment. Nature Biotechnology 1992, 10, 163-167.
Baneyx F. Recombinant protein expression in *Escherichia coli.* Current Opinion in Biotechnology, 1999, 10, 411-421.
Buchner J., Rudolph R., Renaturation, purification and characterization of recombinant Fab-fragments produced in *Escherichia coli.* Nature Biotechnology 1991, 9, 157-162.
Lilie H., Schwarz E., Rudolph R., Advances in refolding of proteins produced in *E. coli.* Current Opinion in Biotechnology 1998, 9, 497-501.
Bradford M., A rapid and sensitive method for the quantitation of microgram quantities of protein utilizing the principle of protein-dye binding. Analytical Biochemistry 1976, 72, 248-254.

(Continued)

*Primary Examiner* — Olga N Chernyshev
(74) *Attorney, Agent, or Firm* — K&L Gates LLP

(57) ABSTRACT

The present invention provides an improved process for inducing the expression of the light chain and heavy chain of the said rHu biosimilar Ranibizumab by employing natural sugars such as lactose and galactose. The replacement of IPTG with natural sugars overcomes the regulatory limitation of synthetic element trace contamination in the final drug substance and reduces the burden on the recombinant host cell.

19 Claims, 8 Drawing Sheets

Specification includes a Sequence Listing.

(56) References Cited

OTHER PUBLICATIONS

Laemmli UK., Cleavage of Structural Proteins during the Assembly of the Head of Bacteriophage T4. Nature 1970, 227, 680-685.
Rathore A., Bhambare R., Establishing analytical comparability for "biosimilars": filgrastim as a case study. Analytical and Bioanaiyticai Chemistry 2014, 406, 6589-6576.

* cited by examiner

SEQUENCE LISTING

<160> NUMBER OF SEQ ID NOS: 4

<210> SEQ ID NO 1
<211> LENGTH: 721
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gagctcatat ggaagttcag ctggttgaaa gcggtggtgg tctggttcag cctggtggta     60
gcctgcgtct gagctgtgca gcaagcggtt atgattttac ccattatggt atgaattggg    120
ttcgtcaggc accgggtaaa ggtctggaat gggttggttg gattaatacc tataccggtg    180
aaccgaccta tgcagcagat tttaaacgtc gttttacctt tagcctggat accagcaaaa    240
gcaccgcata tctgcagatg aatagcctgc gtgcagagga taccgcagtg tattattgtg    300
caaaatatcc gtattattac ggcaccagcc attggtattt cgatgtttgg ggtcagggca    360
ccctggttac cgttagcagc gcaagcacca aaggtccgag cgttttccg ctggcaccga    420 gcagcaaaag taccagcggt ggcaccgcag cactgggttg tctggttaaa gattattttc    480
cggaaccggt taccgtgagc tggaatagcg gtgcactgac cagcggtgtt catacctttc    540
cggcagttct gcagagcagc ggtctgtata gcctgagcag cgttgttacc gttccgagca    600
gcagcctggg cacccagacc tatatttgta atgttaatca taaaccgagc aataccaaag    660
tggataaaaa agtggaaccg aaaagctgcg ataaaaccca tctgtaatag ctcgagccgc    720
g                                                                    721

<210> SEQ ID NO 2
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide sequence of heavy chain of Ranibizumab

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
                210                 215                 220

Ser Cys Asp Lys Thr His Leu
225                 230

<210> SEQ ID NO 3
<211> LENGTH: 669
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gagctccatg gatattcagc tgacccagag cccgagcagc ctgagcgcaa gcgttggtga      60
tcgtgttacc attacctgta gcgcaagcca ggatattagc aattatctga attggtatca     120
gcagaaaccg ggtaaagcac cgaaagtgct gatctatttt accagcagcc tgcatagcgg     180
tgttccgagc cgttttagcg gtagcggtag tggcaccgat tttaccctga ccattagcag     240
cctgcagccg gaagattttg caacctatta ttgtcagcag tatagcaccg ttccgtggac     300
ctttggtcag ggcaccaaag ttgaaattaa acgtaccgtt gcagcaccga gcgtttttat     360
ctttccgcct agtgatgaac agctgaaaag cggcaccgca agcgttgttt gtctgctgaa     420
taacttttat ccgcgtgaag caaaagttca gtggaaagtt gataatgcac tgcagagcgg     480
taatagccaa gaaagcgtta ccgaacagga tagcaaagat agcacctata gcctgagcag     540
caccctgacc ctgagcaaag cagattatga aaaacacaaa gtgtatgcct gcgaagttac     600
ccatcagggt ctgagcagtc cggttaccaa aagtttttaat cgtggtgaat gctaatagaa     660
gcttggtac                                                             669

<210> SEQ ID NO 4
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide sequence of Light chain of Ranibizumab

<400> SEQUENCE: 4

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```

IPTG-FREE INDUCTION PROCESS FOR EXPRESSION OF BIOSIMILAR RHU RANIBIZUMAB ANTIBODY FRAGMENT USING E. COLI

CROSS-REFERENCE TO RELATED APPLICATIONS

The present application is a continuation of U.S. patent application Ser. No. 16/685,041 filed Nov. 15, 2019, which is continuation-in-part of International PCT Application No. PCT/IN2018/050315 filed on May 18, 2018 which claims priority to Indian Patent Application No. 201711017654 filed on May 19, 2017, the entire contents of which are hereby incorporated by reference in their entireties.

SEQUENCE LISTING

The instant application contains a Sequence Listing which has been filed electronically in ASCII format and is hereby incorporated by reference in its entirety. Said ASCII copy, created on Jan. 15, 2020, is named 0815211_00018_SL.txt and is 6,853 bytes in size.

FIELD OF THE INVENTION

The present invention relates to a process for producing refolded recombinant humanized (rHu) Ranibizumab, such that the said process employs natural sugars for inducing the expression of the light chain and heavy chain of the said recombinant humanized Ranibizumab using a duet vector.

More particularly, the present invention relates to a process for inducing the expression of the light chain and heavy chain of the said recombinant humanized Ranibizumab by employing natural sugars such as lactose and galactose.

BACKGROUND AND PRIOR ART OF THE INVENTION

IPTG is most commonly used as an inducer for the expression of rHu Ranibizumab and other recombinant therapeutic proteins. High cost and increased metabolic burden leading to considerable damage to the expression host are some of the critical drawbacks associated with the use of IPTG in existing processes. IPTG is not a naturally occurring compound and "trace contaminations" (ppm) may potentially be of concern to various regulatory authorities.

IPTG used for induction is not an innocuous inducer; instead, it causes damage to the *E. coli* BL21 (DE3) host, which bears a metabolic burden due to its content of plasmids carrying the genes of the recombinant protein to be overexpressed.

Replacing IPTG with natural sugar effector molecules helps to reduce the metabolic stress on bacterial cells and lead to higher biomass and protein yield. An antibody fragment is more complicated than other recombinant proteins; therefore, the induction strategy that works for other recombinant proteins may not give positive results with the former.

The process for parent Indian Patent Application to the present invention relates to novel cloning, expression and refolding process for preparing antibody fragments. The process for inducing the expression of the light and heavy chains of Ranibizumab employs the addition of IPTG.

Due to the encumbrances observed by a person skilled in the art, while employing IPTG as an inducing agent, there is a need to replace IPTG with naturally occurring sugars.

Donovan R. S. et al in a research article titled, 'Optimizing the expression of a monoclonal antibody fragment under the transcriptional control of the *Escherichia coli* lac promoter', published in Can J Microbiol. 2000 June; 46(6):532-41, compares the expression of a monoclonal antibody Fab fragment in *Escherichia coli* strain RB791/pComb3, induced with either lactose or isopropyl-beta-D-thiogalactopyranoside (IPTG), to determine if lactose might provide an inexpensive alternative to induction with IPTG. Moreover, Donovan R. S. employ a lac promoter for periplasmic expression of Fab.

It is therefore evident from above, that there have been no attempts in prior art disclosures reporting the use of lactose or galactose for the cytoplasmic expression of recombinant humanized (rHu) Ranibizumab antibody fragment in a recombinant host cell such that the yield of the said antibody fragments is increased.

OBJECT OF THE INVENTION

It is an object of the present invention to provide for a process for induction for the expression of the light and heavy chains of rHu Ranibizumab by employing a combination of sugars to prevent damage and burden to the host cell.

It is another object of the present invention to provide a process for producing rHu antibody fragments by inducing the T7 promoter system for the expression of light and heavy chains of rHu Ranibizumab.

SUMMARY OF THE INVENTION

Accordingly the present invention provides an improved process for inducing the expression of light and heavy chains of recombinant humanized (rHu) Ranibizumab antibody fragments in a host cell, characterized in that the said process comprising co-expressing light and heavy chains of the said antibody fragments into the host cell cytoplasm in approximately equal proportions in the presence of inducing agents selected from the group comprising lactose and galactose to obtain inclusion bodies.

In a preferred embodiment, the inducing agent is present in a concentration ranging from 1 mM to 50 mM.

In an embodiment the said host cell is *E. coli*.

In an embodiment the said *E. coli* is *E. coli* BL21 (DE3).

The present invention also provides an improved process for producing refolded recombinant humanized Ranibizumab by employing the process for inducing the expression of light and heavy chains of recombinant humanized (rHu) Ranibizumab, the said process comprising;
(a) transforming vectors carrying nucleotide sequence having SEQ ID No: 1 and SEQ ID No: 3 encoding heavy chain and light chain of antibody fragments, respectively, in host cells;
(b) subjecting the host cells to high cell density fermentation;
(c) co-expressing light and heavy chains of said antibody fragment into the host cell cytoplasm in approximately equal proportions by induction in the presence of sugars selected from lactose and galactose to obtain inclusion bodies; and
(d) refolding of light and heavy chains of antibody fragments.

In an embodiment the said process comprises expression of light and heavy chains of rHu Ranibizumab by inducing a T7 promoter system.

In another embodiment the said process further comprises;
(a) Solubilizing the inclusion bodies containing an approximately equal proportion of light and heavy chains of recombinant antibody fragments in the presence of a solubilization buffer to obtain solubilized light and heavy chains of antibody fragments;
(b) Refolding the solubilized light and heavy chains of antibody fragments by diluting a denaturant followed by oxygenation in the presence of an oxidizing agent to trigger oxidation of disulfide bond to obtain biologically active form of rHu Ranibizumab; and
(c) Subjecting rHu Ranibizumab obtained in step (b) to ultra-filtration by using 5 KDa tangential flow filtration device

DETAILED DESCRIPTION OF DRAWINGS

DETAILED DESCRIPTION OF THE INVENTION

The invention will now be described in detail in connection with certain preferred and optional embodiments, so that various aspects thereof may be more fully understood and appreciated.
Source of Biological Material:
*E. coli* BL21 (DE3) cells purchased from Merck Millipore Life Science Private Limited, India.
In a preferred embodiment, the present invention provides an improved process for inducing the expression of light and heavy chains of recombinant humanized Ranibizumab antibody fragments in a host cell, the said process comprising co-expressing the said light and heavy chains of the said antibody fragments into the host cell cytoplasm in approximately equal proportions in the presence of inducing agents such as sugars selected from the group comprising lactose and galactose to obtain inclusion bodies.

In another preferred embodiment, the present invention provides an improved process for producing refolded recombinant humanized Ranibizumab, the said process comprising;
(a) transforming vectors carrying nucleotide sequence having SEQ ID No: 1 and SEQ ID No: 3 encoding heavy chain and light chain of antibody fragments, respectively, in host cells;
(b) subjecting the host cells to high cell density fermentation,
(c) co-expressing light and heavy chains of said antibody fragments into the host cell cytoplasm in approximately equal proportions by induction in the presence of lactose and/or galactose to obtain inclusion bodies, and
(d) refolding of light and heavy chains of antibody fragments.

The nucleotide sequence represented by Seq Id No. 1 encodes the heavy chain of Ranibizumab represented by Seq Id No. 2. The nucleotide sequence represented by Seq Id No. 3 encodes the light chain of Ranibizumab represented by Seq Id No. 4.

In accordance with the aforesaid embodiment, the present invention provides inducing agents selected from natural sugars, viz., lactose and galactose in a concentration ranging from 1 mM to 50 mM.

In an embodiment, the present invention provides the host cell is selected from recombinant *E. coli*, more preferably an *E. coli* BL 21(DE3) expression system.

In another embodiment, the present invention provides solubilization is carried out in the presence of a solubilization buffer comprising Tris buffer in a concentration ranging from 0.1 M to 0.5 M with pH in the range of 7 to 10. The concentration of EDTA is ranging from 1 mM to 4 mM and that of guanidine hydrochloride is in the range from about 3 M to about 6 M.

Accordingly, the solubilization preferably comprises 0.1 M Tris pH 9.0, 2 mM EDTA and 6 M guanidine hydrochloride and further reduced with Dithiothreitol (DTT).

Figure 3:
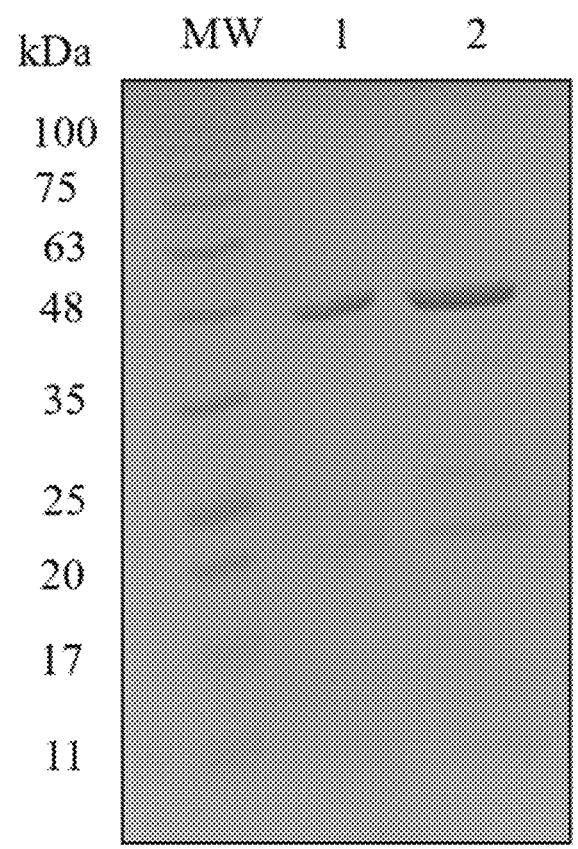
FIG. 3 depicts the SDS-PAGE analysis of refolded and partially purified rHu Ranibizumab under non-reducing conditions. Lane MW: Molecular marker, Lane 1: Innovator rHu Ranibizumab, Lane 2: CSIR-NCL rHu Ranibizumab.
Figure 5:
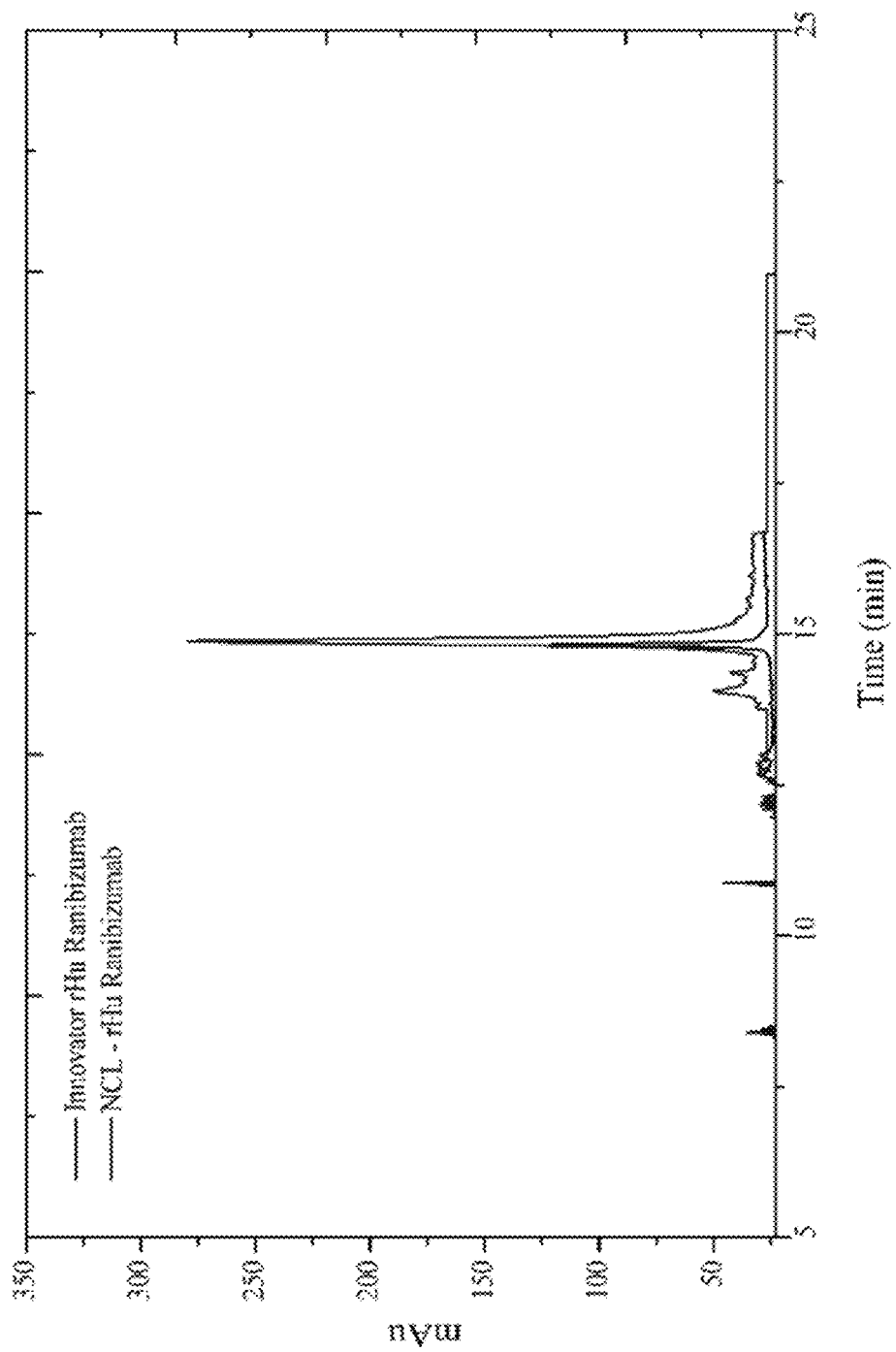
FIG. 5 depicts the RP-HPLC analysis overlay of refolded and purified rHu biosimilar Ranibizumab with an innovator Ranibizumab molecule under non-reduced conditions.

Inclusion bodies were initially solubilized in solubilization buffer containing 0.1 M Tris pH 9.0, 2 mM EDTA and 6 M Guanidine hydrochloride as a denaturant for 30 minutes followed by addition of 5 mM DTT and kept for reduction for an hour. This soluble and reduced inclusion body solution was kept for oxidation by adding 10 mM oxidized glutathione. This was followed by refolding using 75 fold dilution at 10±2° C. in the refolding buffer containing 0.1 M Tris pH 9.0, 0.6 M Arginine, 5% Sorbitol, 2 mM EDTA. Oxidative refolding was also carried out by passing pure oxygen by 1 SLPM (Standard liter per minute) flow rate into in vitro refolding process. Oxygen triggered the formation of disulfide bond and rate of the reaction by oxidation of thiol group in cysteine amino acid. Redox shuffle was also used and it formed a mixed disulfide bond with cysteine amino acid of protein followed by a nucleophilic attack which allowed the formation of correct disulfide bonds between cysteine amino acids of the protein molecule. Refolding output was subjected to ultra-filtration by using 5 kDa Ultrasette™ Lab Tangential Flow Filtration devise followed by buffer exchanged into 20 mM Tris pH 9.0. Refolded rHu Ranibizumab was observed on non-reducing 12% SDS- PAGE at 48 kDa (FIG. 3). The quantity and quality of refolded rHu Ranibizumab was measured by reverse phase HPLC (FIG. 5).

In yet another preferred embodiment, the present invention provides an increase in the total Ranibizumab yield in concentrations ranging from 2.3 g/L to 3 g/L in a 1 L bioreactor scale.

High cell density E. coli fermentation lead to an optical density of ~95.0 to 110.0 at 600 nm with about ~51.0 to 55.0 g/l biomass (DCW) leading to the generation of about 15.20 g/l and 18.70 g/l inclusion bodies in case of lactose and galactose-based induction respectively.

In the case of IPTG based induction using identical process parameters, the inclusion body yield was obtained to be 17.0 g/l. Target protein yield obtained in a fed-batch process at the bioreactor scale was found to be 2.30 g/l and 2.81 g/l in case of lactose and galactose-based induction respectively, as compared to 2.04 g/l obtained in case of IPTG based induction.

Figure 1:
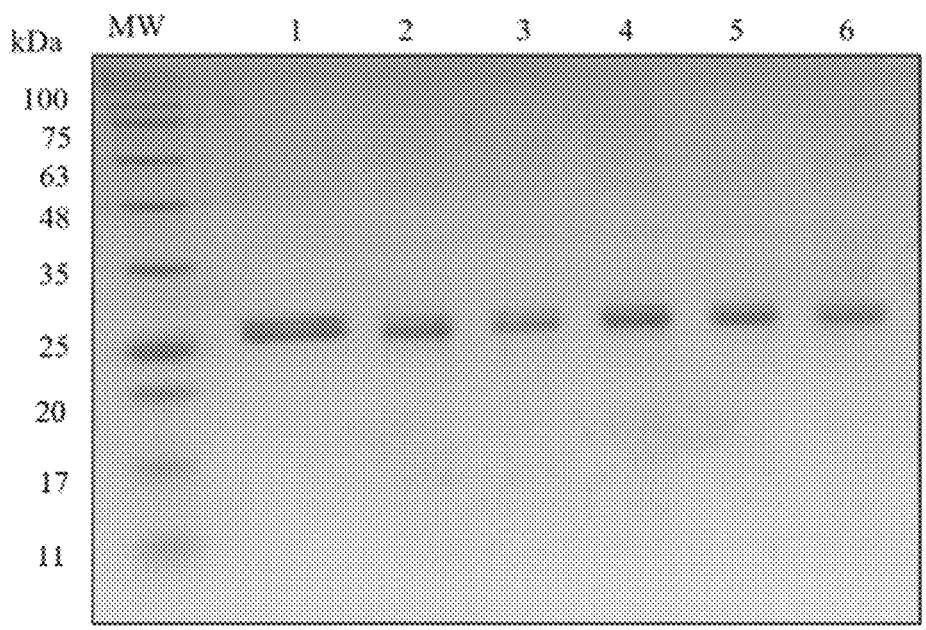
FIG. 1 depicts SDS-PAGE analysis for light and heavy chain of rHu Ranibizumab expressed using galactose as an inducer under reducing conditions. Lane MW: Molecular marker, Lane 1: Innovator rHu Ranibizumab (Lucentis), Lane 2: 1 mM galactose, Lane 3: 5 mM galactose, Lane 4: 15 mM galactose, Lane 5: 30 mM galactose, Lane 6: 50 mM galactose.
Figure 2:
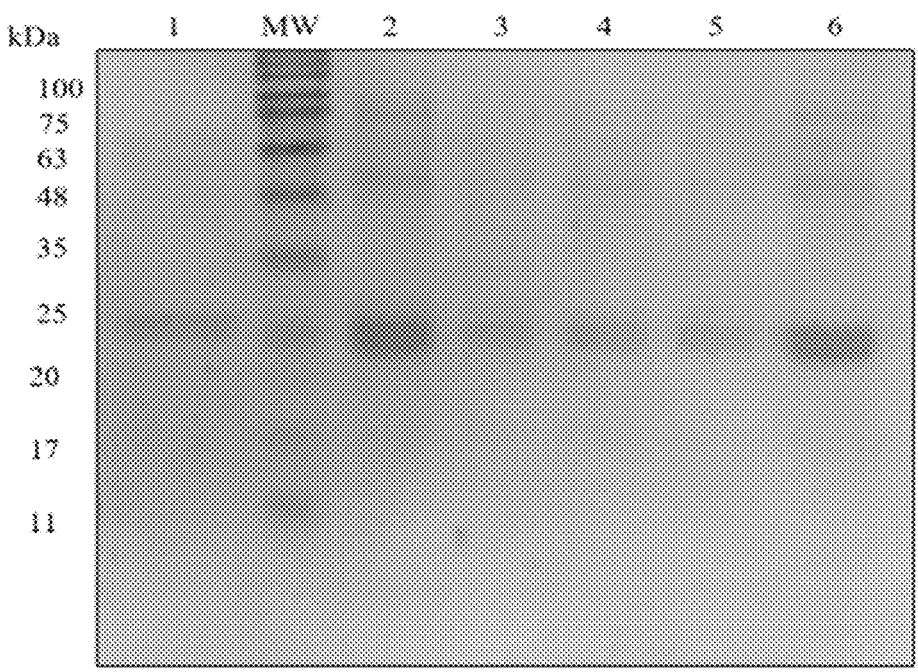
FIG. 2 depicts SDS-PAGE analysis for light and heavy chain of rHu Ranibizumab expressed using of using lactose as an inducer under reducing conditions. Lane MW: Molecular marker, Lane 1: Innovator rHu Ranibizumab (Lucentis), Lane 2: 1 mM lactose, Lane 3: 5 mM lactose, Lane 4: 15 mM lactose, Lane 5: 30 mM lactose, Lane 6: 50 mM lactose.

FIGS. 1 and 2 shows the expression of the light chain and heavy chain using duet vector with galactose and lactose as inducers respectively, which conformed approximately equal expression of both chains.

EXAMPLES

The following examples are given by way of illustration of the present invention and therefore should not be construed to limit the scope of the present invention.

Example 1: Cloning (i) Light Chain and Heavy Chain Nucleotide Sequence Construction by Codon Optimization
  Amino acid sequences of the light chain and heavy chain were taken from drug bank (Accession No.: DB01270) and codon optimization was performed.
(ii) Generation of pRSF Duet Vector for Light Chain and Heavy Chain of rHu Ranibizumab
  Bacterial expression vector pRSF duet vector was constructed by cloning light chain nucleotide sequence ID No. 3 at 5' end into NcoI/HindIII cloning site preceding by T7 promotor in multiple cloning site I (MCS I) and heavy chain nucleotide sequence at 5' end into NdeI/XhoI cloning site preceding by T7 promotor in multiple cloning site II (MCS II).
(iii) Transformation of Genes for Light Chain and Heavy Chain in E. coli BL 21 (DE3) Expression System
  pRSF duet vector having light chain gene and heavy chain gene construct was transformed with competent BL 21(DE3) expression system. Transformation method comprises: Mixture of vector and host was incubated for 30 min on ice and then heat shock at 42° C. was given for 35 seconds. Again cells were incubated on ice for 15 minutes. 800 ul of SOC medium was added and incubated for 1 hour and 45 minutes at 450 rpm. Transformed cells were centrifuged at 2000 rpm for 5 minutes. BL21 (DE3) E. coli transformants were plated on 30 μg/ml kanamycin containing LB agar plates. Transformed cells containing plates were incubated at 37° C. for overnight. Next day, a colony of transformed BL21 (DE3) was selected for protein expression in the host cell.

Example 2: rHu Ranibizumab Expression at Shake Flask Level Using Galactose

Figure 4:
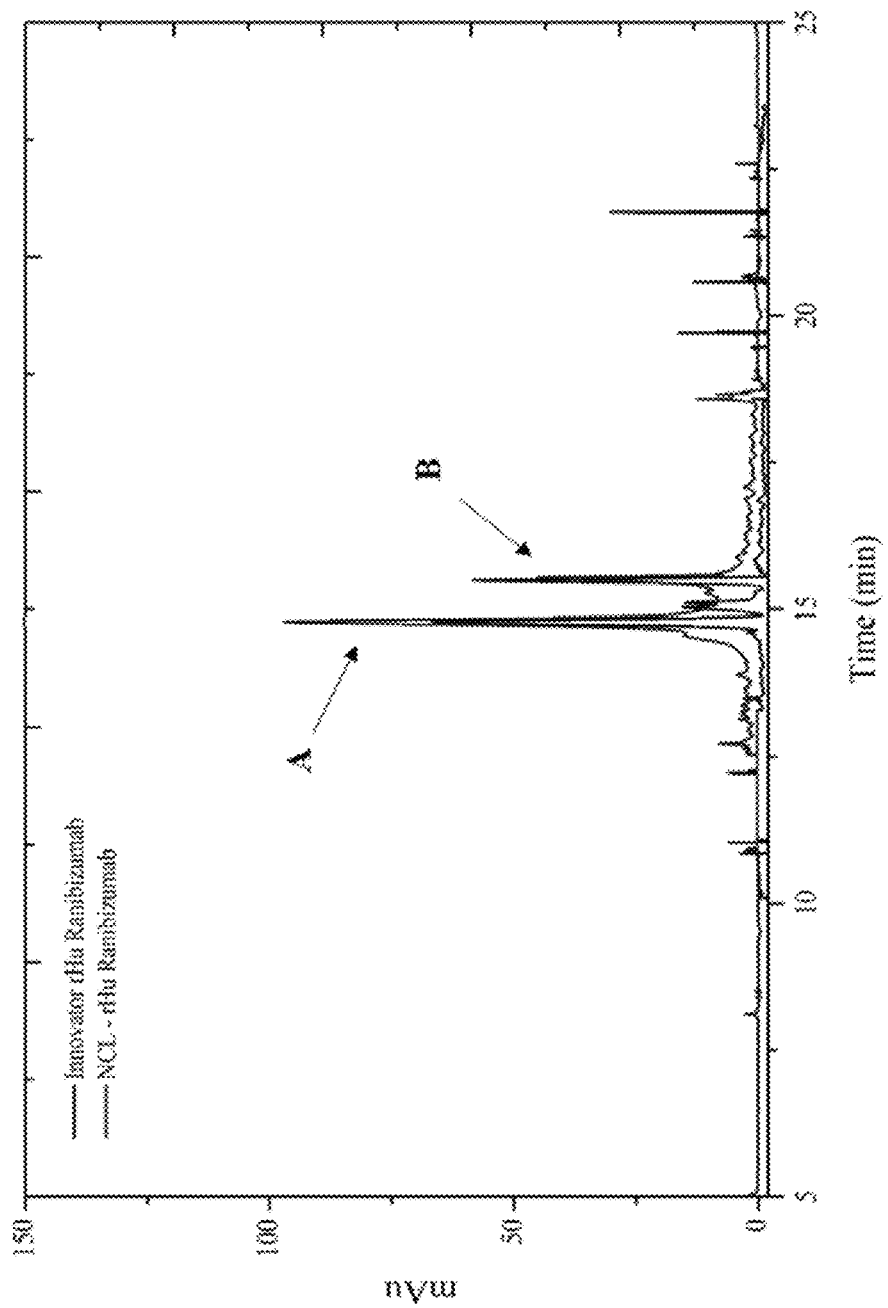
FIG. 4 depicts the RP-HPLC analysis overlay of the target protein rHu biosimilar Ranibizumab with the innovator molecule under reduced and alkylated conditions (A: Light chain, B: Heavy chain)

Selected transformants of BL21 (DE3) cells were tested for rHu Ranibizumab expression. The selected colonies were inoculated into 50 ml terrific broth with 30 μg/ml kanamycin. Cells were grown until the optical density at 600 nm reached about 1 to 1.5. 5 ml of these well-grown colonies were transformed into 100 ml terrific media and incubated at 37° C. and 225 rpm. After achieving an optical density of 1.0-1.5 at 600 nm the E. coli culture was induced with various concentrations of galactose viz. 1 mM, 5 mM, 15 mM, 30 mM, and 50 mM. Cells were harvested after a 12 hour induction and centrifuged at 6000 rpm for 30 min. The supernatant was discarded and the cell pellet was re-suspended in 100 mM Tris, 0.1 mM EDTA pH 9.0 lysis buffer. Cells were lysed in highpressure homogenizer at 15000 bar pressure for 10 minutes. Lysed cells were centrifuged at 6000 rpm for 25 minutes. Presence of expressed protein in the pellet obtained postlysis was checked using SDS-PAGE analysis under reducing conditions. FIG. 1 shows the expression of the light chain and heavy chain using duet vector with galactose which conformed approximately equal expression of both chains. Shake flask level E. coli fermentation lead to an optical density of 3.14±0.21 at 600 nm corresponding to 5.57±0.19 g/l biomass. The quantity and purity of light and heavy chain of rHu Ranibizumab in inclusion body was measured by reverse phase HPLC (FIGS. 4 and 5). The optimized fermentation conditions were scaled up and replicated at the 1 L bioreactor scale.

Example 3: rHu Ranibizumab Expression at Shake Flask Level Using Lactose

Selected transformants of BL21 (DE3) cells were tested for rHu Ranibizumab expression. The selected colonies were inoculated into 50 ml terrific broth with 30 μg/ml kanamycin. Cells were grown until the optical density at 600 nm reached about 1 to 1.5. 5 ml of these well-grown colonies were transformed into 100 ml terrific media and incubated at 37° C. and 225 rpm. After achieving an optical density of 1.0-1.5 at 600 nm the E. coli culture was induced with concentrations of lactose viz. 1 mM, 5 mM, 15 mM, 30 mM, and 50 mM. Cells were harvested after a 12-hour induction and centrifuged at 6000 rpm for 30 min. The supernatant was discarded and the cell pellet was re-suspended in 100 mM Tris, 0.1 mM EDTA pH 9.0 lysis buffer. Cells were lysed in high-pressure homogenizer at 15000 bar pressure for 10 minutes. Lysed cells were centrifuged at 6000 rpm for 25 minutes. Presence of expressed protein in the pellet obtained post-lysis was checked using SDS-PAGE analysis under reducing conditions. FIG. 2 shows the expression of the light chain and heavy chain using duet vector with lactose which conformed approximately equal expression of both chains. Shake flask level E. coli fermentation lead to an optical density of 3.12±0.08 at 600 nm corresponding to 5.47±0.09 g/l biomass. The quantity and purity of light and heavy chain of rHu Ranibizumab in inclusion body was measured by reverse phase HPLC (FIGS. 4 and 5). The optimized fermentation conditions were scaled up and replicated at the 1 L bioreactor scale.

Example 4: rHu Ranibizumab Expression at Bioreactor Level

Protein expression was carried out in a 1 L bioreactor. Selectively transformed BL21 (DE3) cells were evaluated for rHu Ranibizumab expression. The selected colonies were inoculated into 50 ml terrific broth with 30 μg/ml kanamycin. Cells were grown until the optical density at 600 nm reached in between 1.0 to 1.5. 5 ml of these well-grown colonies were transformed into 100 ml of terrific broth and incubated it at 37° C. and 225 rpm. 100 ml seed culture was transformed into 900 ml terrific media. High cell density fermentation in a fed-batch mode was carried out by using BioFlo®/CelliGen®115 benchtop fermenter with an automatic gas mixture at 1 SLPM gas flow range by using 2 L heat blanketed glass vessels with baffles assembly having direct drive motor, two Rushton impellers and ring sparger (Macrosparger). Automatic DO cascade agitation, GasFlo and the 02 mix was selected with a DO setpoint of 30%. Agitation cascade lower limit was kept at 300 rpm and the higher limit was kept at 1000 rpm. GasFlo cascade was kept at 1 SLPM and 02 mix was kept 0-80%. *E. coli* culture was induced with lactose in one experiment and galactose in another experiment at mid-log phase. Cells were harvested after 9 hours of induction and the culture broth was centrifuged at 6000 rpm for 30 minutes. The supernatant was discarded and the cell pellet was re-suspended in 100 mM Tris, 0.1 mM EDTA pH 9.0 lysis buffer. Cells were lysed in high-pressure homogenizer for 10 min at 15000 bar pressure. Lysed cells were centrifuged at 6000 rpm for 25 minutes. Presence of the expressed rHu Ranibizumab in the pellet obtained post cell lysis was determined using SDS-PAGE analysis. High cell density *E. coli* fermentation lead to an optical density of ~95.0 to 110.0 at 600 nm with about ~51.0 to 55.0 g/l biomass (DCW) leading to the generation of about 15.20 g/l and 18.70 g/l inclusion bodies in case of lactose and galactose-based induction respectively. In the case of IPTG based induction using identical process parameters, the inclusion body yield was obtained to be 17.0 g/l. Target protein yield obtained in a fed-batch process at the bioreactor scale was found to be 2.30 g/l and 2.81 g/l in case of lactose and galactose-based induction respectively, as compared to 2.04 g/l obtained in case of IPTG based induction.

TABLE 1

Target protein yield and inclusion body yield at the 1 L bioreactor scale using different induction strategies in a fed-batch process.

| Inducers | Total protein yield (HC + LC) (g $L^{-1}$) | Inclusion body yield (g $L^{-1}$) |
|---|---|---|
| IPTG | 2.04 | 17.0 |
| Lactose | 2.30 | 15.2 |
| Galactose | 2.81 | 18.7 |

Example 5: Pretreatment for Inclusion Bodies of the Light Chain and Heavy Chain of rHu Ranibizumab and Subsequent Refolding Inclusion bodies were initially solubilized in solubilization buffer containing 0.1 M Tris pH 9.0, 2 mM EDTA and 6M Guanidine hydrochloride as a denaturant for 30 minutes followed by addition of 5 mM DTT and kept for reduction for an hour. This soluble and reduced inclusion body solution was kept for oxidation by adding 10 mM oxidized glutathione. This was followed by refolding using 75 fold dilution at 10±2° C. in the refolding buffer containing 0.1 M Tris pH 9.0, 0.6 M Arginine, 5% Sorbitol, 2 mM EDTA. Oxidative refolding was also carried out by passing pure oxygen by 1 SLPM (Standard liter per minute) flow rate into in vitro refolding process. Oxygen triggered the formation of disulfide bond and rate of the reaction by oxidation of thiol group in cysteine amino acid. Redox shuffle was also used and it formed a mixed disulfide bond with cysteine amino acid of protein followed by a nucleophilic attack which allowed to formcorrect disulfide bonds between cysteine amino acids of the protein molecule. Refolding output was subjected to ultra-filtration by using 5 kDa Ultrasette™ Lab Tangential Flow Filtration devise followed by buffer exchanged into 20 mM Tris pH 9.0. Refolded rHu Ranibizumab was observed on non-reducing 12% SDS-PAGE at 48 kDa (FIG. 3). The quantity and quality of refolded rHu Ranibizumab were measured by reverse phase HPLC (FIG. 5).

Example 6: Analytical Characterization of Expressed Light and Heavy Chains of Recombinant rHu Ranibizumab (i) Absorbance Measurement at A280 for rHu Ranibizumab Samples Total protein in solubilization and refold outputs was determined using UV absorbance measurement at 280 nm. All fractions collected were read at 280 nm using Nanodrop™ 2000 and UV-1800 Shimadzu UV Visible spectrophotometer.

(ii) SDS PAGE Analysis of rHu Ranibizumab Samples

SDS PAGE analysis for identification of expression of light chain and heavy chain of rHu Ranibizumab was carried out using 12% (Thickness 1 mm) of the resolving gel under reducing condition (FIGS. 1 and 2) and refolded rHu Ranibizumab was observed on non-reducing SDS-PAGE (FIG. 3) at the stacking gel constant voltage 120V and resolving gel constant voltage 100V conditions. Each sample was boiled for 10 min in the starting buffer before being loaded into the gel. 0.05% (w/v) Coomassie brilliant blue G-250 in 4:1:5 (Water: Glacial Acetic acid: Methanol) was used to detect proteins after electrophoretic separation on polyacrylamide gels.

(iii) Reverse Phase HPLC Analysis of rHu Ranibizumab

The inclusion bodies obtained post primary washing steps were subjected to solubilization in the aforementioned solubilization buffer and reduced with 10 mM DTT to break down the disulfide bridges. This was followed by alkylation using 20 mM Iodoacetamide (IAA) to covalently modify cysteine SH-groups, preventing them from forming unwanted novel disulfide bonds. Quantitative and qualitative analysis of rHu Ranibizumab was performed using reverse phase chromatography under reduced and alkylated conditions (FIG. 4) as well as refolded conditions using 4.6 mm×50 mm Poroshe11120 EC-C18 2.7 μm column on Agilent 1260 HPLC system. The mobile phase consisted of 0.1% (v/v) TFA in water (solvent A) and 0.1% (v/v) TFA, 70% (v/v) of acetonitrile and 30% isopropyl alcohol (solvent B). The flow rate was maintained at 1 ml/min using a linear gradient of A to B at a wavelength of 214 nm. FIG. 5 shows RP-HPLC chromatogram of innovator and refolded rHu Ranibizumab.

(iv) Intact Mass Analysis of Refolded rHu Ranibizumab by Matrix-Assisted Laser Desorption/Ionization (MALDI-TOF) (Time-of-Flight Mass Spectrometer)

Figure 6:
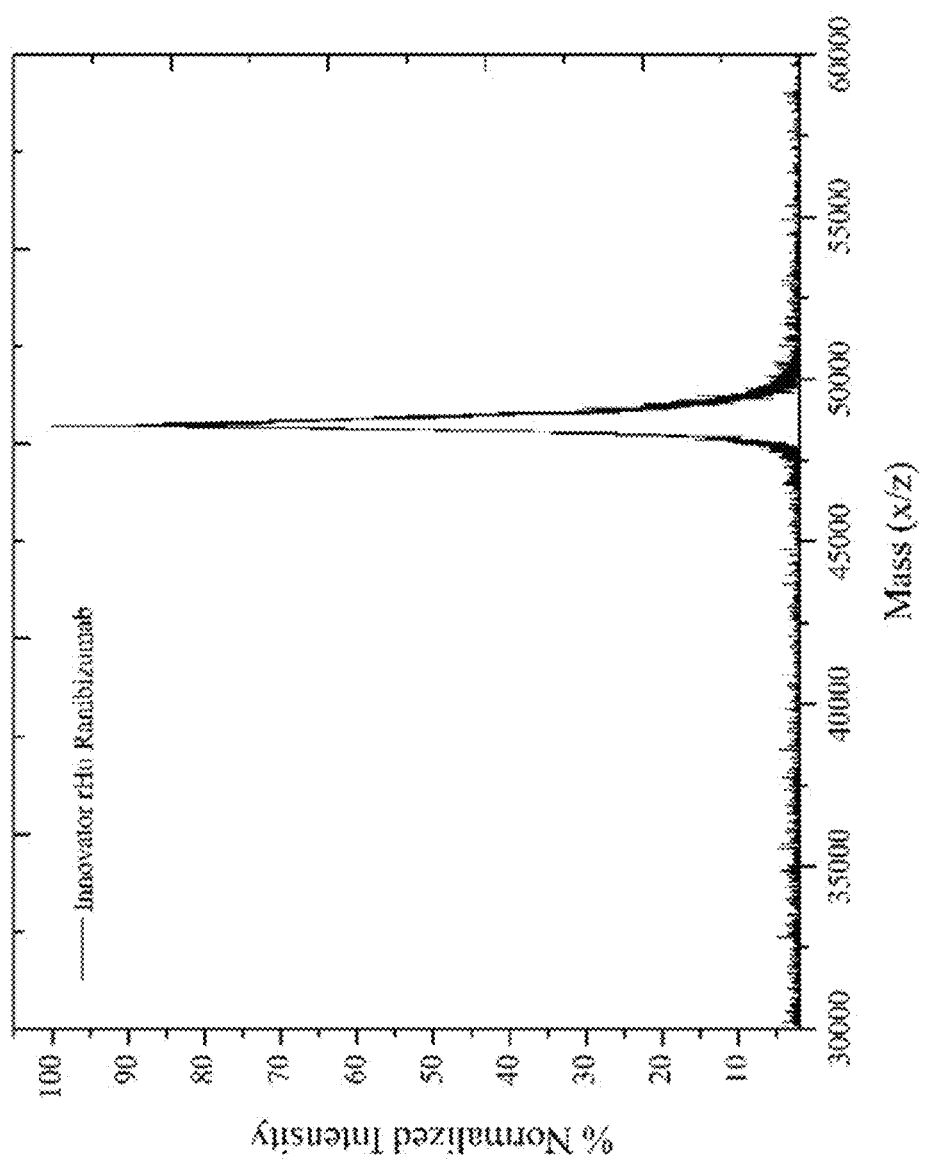
FIG. 6 depicts intact mass analysis of innovator molecule and under non-reduced conditions using MALDI-TOF MS.
Figure 7:
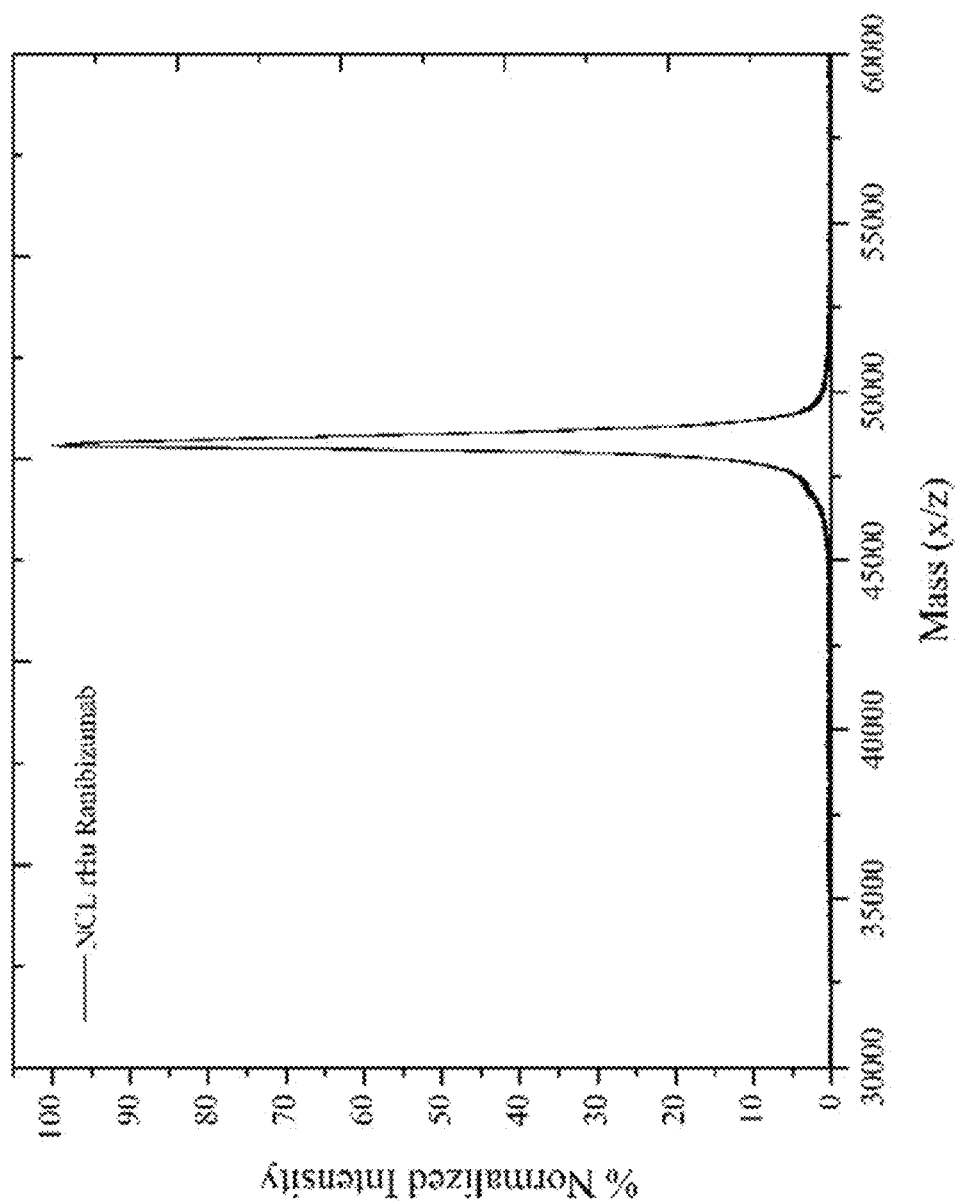
FIG. 7 depicts the intact mass analysis of refolded and purified rHu Ranibizumab under non-reduced conditions using MALDI-TOF MS.
Figure 8:
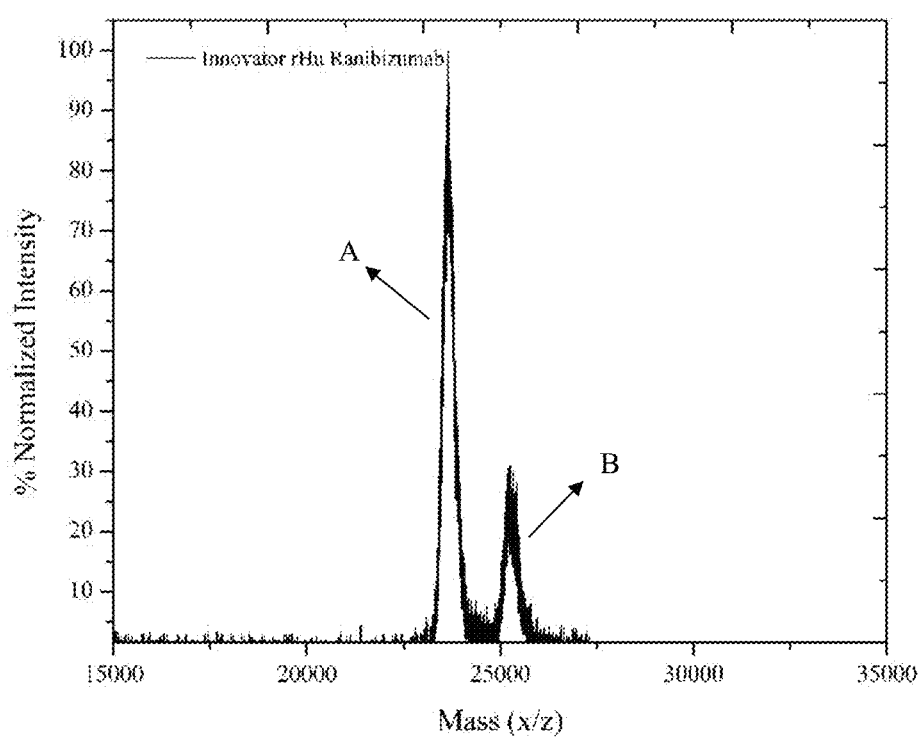
FIG. 8 depicts the MALDI-TOF MS analysis of the innovator molecule under reduced and alkylated conditions. (A: Light chain, B: Heavy chain)
Figure 9:
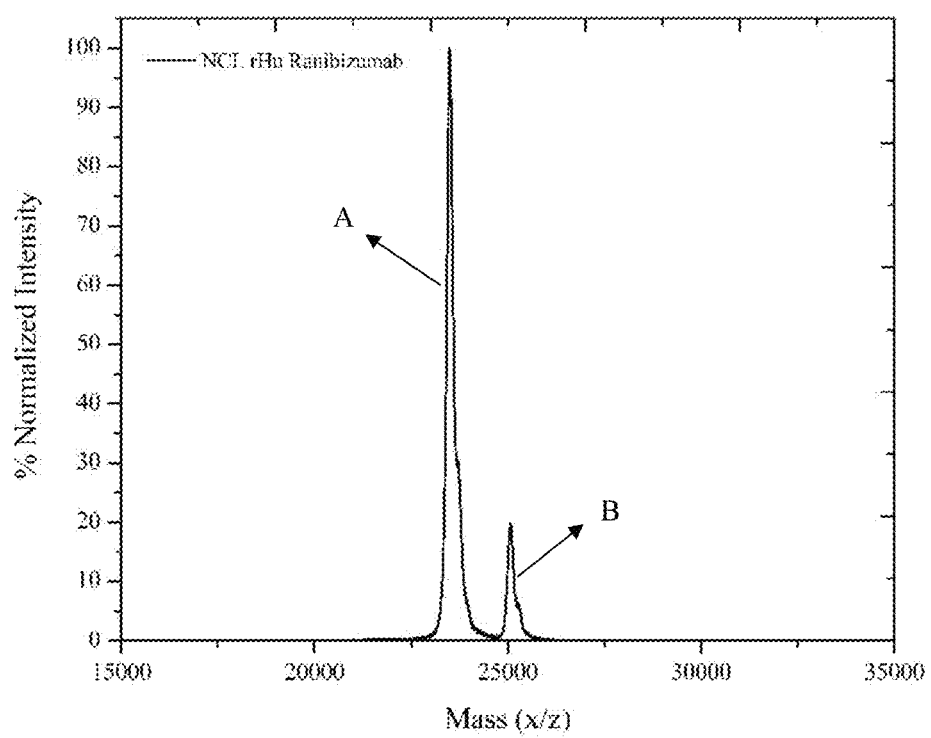
FIG. 9 depicts a MALDI-TOF MS analysis of refolded and purified rHu Ranibizumab compared under reduced and alkylated conditions. (A: Light chain, B: Heavy chain).

Standard and refolded purified rHu Ranibizumab with sinapinic acid matrix was mixed in 1:1 ratio to perform MALDI-TOF analysis (FIGS. 6 and 7). Similarly, reduced and alkylated standard and refolded rHu Ranibizumab was mixed with sinapinic acid matrix in 1:1 ratio to perform MALDI-TOF analysis (FIGS. 8 and 9). Matrix sinapinic acid (10 mg/mL) was prepared in 50% v/v acetonitrile, 0.1% v/v TFA in high purity water. 1 µl of the homogenized mixture of sample and matrix was deposited on a clean 384 well MALDI plate. The plate was inserted into AB SCIEX TOF/TOF™ 5800 instrument. The instrument was used in positive ion mode. Nitrogen laser at 337 nm radiation was kept as an ionization source. Laser intensity in between 4000 to 5000 was used for the analysis of samples. Result analysis was performed using Data Explorer® Software Version 4.11. FIGS. 6 and 7 shows a comparison of the intact mass of refolded rHu Ranibizumab with innovator rHu Ranibizumab under non-reduced conditions. FIGS. 8 and 9 shows light chain and heavy chain of purified rHu Ranibizumab mass comparability with reduced and alkylated innovator rHu Ranibizumab.

Advantages of the Invention

At efficient inducing dosages, the cost of IPTG is approximately hundredfold of lactose, therefore using lactose as an inducing agent has industrially remarkable advantages.

Galactose is not metabolized by *E. coli* BL21 (DE3) and acts more specifically as compared to lactose. The cost of IPTG is approximately 15 to 20 fold of galactose, thus making galactose an economically feasible replacement.

Induction using lactose and galactose leads to comparable and higher protein yield, respectively, as compared to induction using IPTG.

The replacement of IPTG with natural sugars overcomes the regulatory limitation of synthetic element trace contamination in the final drug substance.

We claim:

1. An improved process for inducing expression of light and heavy chains of antibody fragments in a host cell, the process comprising:
co-expressing light and heavy chains of the antibody fragments in the presence of an inducing agent selected from the group consisting of lactose, galactose, and combination thereof to obtain inclusion bodies, wherein vectors carrying nucleotide sequences comprising SEQ ID No: 1 and SEQ ID No: 3 causes the co-expression of the light and heavy chains into the same host cell cytoplasm in approximately equal proportions.

2. The process as claimed in claim 1, wherein the inducing agent is present in a concentration ranging from 1 mM to 50 mM.

3. The process as claimed in claim 1, wherein the host cell is *E. coli*.

4. The process as claimed in claim 3, wherein the *E. coli* is *E. coli* BL21 (DE3).

5. The process as claimed in claim 1, wherein the antibody fragments are of recombinant humanized Ranibizumab.

6. The process as claimed in claim 1, wherein the inducing agent is galactose.

7. The process as claimed in claim 1, wherein the inducing agent is lactose.

8. The process as claimed in claim 1, wherein the inducing agent is present in the concentration ranging from 15 mM to 50 mM.

9. The process as claimed in claim 1, wherein the co-expression of the light and heavy chains of the antibody fragments into the same host cell cytoplasm in approximately equal proportions for each host cell comprises inducing a T7 promoter system.

10. The process as claimed in claim 1, wherein the inducing agent is added in a mid-log phase of the induction.

11. A process for producing refolded recombinant humanized Ranibizumab, the process comprising:
(a) transforming vectors carrying nucleotide sequences comprising SEQ ID No: 1 and SEQ ID No: 3, encoding heavy chain and light chain of antibody fragments, respectively, into host cells;
(b) subjecting the host cells to high cell density fermentation;
(c) co-expressing light and heavy chains of the antibody fragment by induction in the presence of a sugar selected from the group consisting of lactose, galactose, and combination thereof to obtain inclusion bodies, wherein, for each host cell, the respective vector carrying nucleotide sequences comprising SEQ ID No: 1 and SEQ ID No: 3 causes the co-expression of the light and heavy chain into the same host cell cytoplasm in approximately equal proportions;
(d) refolding of light and heavy chains of antibody fragments;
(e) solubilizing the inclusion bodies containing an approximately equal proportion of light and heavy chains of recombinant antibody fragments in the presence of a solubilization buffer to obtain solubilized light and heavy chains of antibody fragments;
refolding the solubilized light and heavy chains of antibody fragments by diluting a denaturant followed by oxygenation using pure oxygen in the presence of an oxidizing agent to trigger oxidation of disulfide bond to obtain biologically active form of rHu Ranibizumab; and
(g) subjecting rHu Ranibizumab obtained in step (f) to ultra-filtration by using 5KDa tangential flow filtration device.

12. The process for producing refolded recombinant humanized Ranibizumab as claimed in claim 5, wherein the process comprises expression of light and heavy chains of rHu Ranibizumab by inducing a T7 promoter system.

13. The process as claimed in claim 11, wherein the sugar is galactose.

14. The process as claimed in claim 11, wherein the sugar is lactose.

15. The process as claimed in claim 11, wherein the sugar is present in a concentration ranging from 15 mM to 50 mM.

16. The process as claimed in claim 11, wherein the sugar is added in a mid-log phase of the induction.

17. The process as claimed in claim 11, wherein the vectors are duet vectors.

18. The process as claimed in claim 11, wherein the oxygenation is conducted using pure oxygen and the oxidizing agent is oxidized glutathione.

19. The process as claimed in claim 11, wherein the solubilization buffer comprises 0.1-0.5 M Tris buffer with pH in a range of 7-10, 1-4 mM EDTA, about 3-6 M Guanidine hydrochloride and a reducing agent.

* * * * *